(12) United States Patent
Nilsson

(10) Patent No.: US 8,697,862 B2
(45) Date of Patent: Apr. 15, 2014

(54) SYNTHESIS OF GALACTOSIDE INHIBITORS

(75) Inventor: Ulf Nilsson, Lund (SE)

(73) Assignee: Galecto Biotech AB, Lund (SE)

( * ) Notice: Subject to any disclaimer, the term of this patent is extended or adjusted under 35 U.S.C. 154(b) by 131 days.

(21) Appl. No.: 12/992,328

(22) PCT Filed: May 18, 2009

(86) PCT No.: PCT/SE2009/050560
§ 371 (c)(1),
(2), (4) Date: Feb. 7, 2011

(87) PCT Pub. No.: WO2009/139719
PCT Pub. Date: Nov. 19, 2009

(65) Prior Publication Data
US 2011/0130553 A1 Jun. 2, 2011

(30) Foreign Application Priority Data

May 16, 2008 (SE) ...................................... 0801119

(51) Int. Cl.
| | | |
|---|---|---|
| C07H 1/00 | (2006.01) | |
| C07H 3/00 | (2006.01) | |
| C08B 37/00 | (2006.01) | |
| C07H 17/02 | (2006.01) | |
| C13K 5/00 | (2006.01) | |
| C13K 7/00 | (2006.01) | |

(52) U.S. Cl.
USPC ...................................................... 536/124

(58) Field of Classification Search
None
See application file for complete search history.

(56) References Cited

U.S. PATENT DOCUMENTS

2006/0148712 A1   7/2006   Liu et al.

FOREIGN PATENT DOCUMENTS

| WO | 99/26956 A1 | 6/1999 |
| WO | 02/057284 A1 | 7/2002 |
| WO | 2005/113568 A1 | 12/2005 |
| WO | 2005/113569 A1 | 12/2005 |

OTHER PUBLICATIONS

El Ashry et al., Journal of Carbohydrate Chemistry, "Synthesis of Interglycosidically S-Linked 1-Thio-Oligosaccharides Under Microwave Irradiation", 2005, vol. 24, pp. 745-753.*
Todd L. Lowary, et al; "Recognition of Synthetic 0-methyl, Epimeric, and Amino Analogues of the Acceptor α-L-Fuc p-(1-→2)-,β-D-Gal-p-OR by the Blood-Group A and B Gene-Specified Glycosyltransferases", Carbohydrate Research, vol. 251 (Jan. 3, 1994) 33-67.
Pernilla Sörme, et al; "Structural and Thermodynamic Studies on Cation-II Interactions in Lectin-Ligand Complexes: High-Affinity Galectin-3 Inhibitors through Fine-Tuning of an Arginine-Arene Interaction", JACS Articles Published on Web Jan. 21, 2005, J. Am. Chem. Soc. 2005, Publication Date (Web): Jan. 21, 2005.
Constance M. John, et al; "Truncated Galectin-3 Inhibits Tumor Growth and Metastasis in Orthotopic Nude Mouse Model of Human Breast Cancer", Clinical Cancer Research 2003; 9:2374-2383. Published online Jun. 1, 2003.
Hakon Leffler, et al; "Introduction to galectins", Glycoconjugate Journal 2004, vol. 19, Issue 7-9, pages 433-440, Publication Date Jan. 1, 2002.
Roland J. Pieters; "Inhibition and Detection of Galectins", ChemBioChem 2006, vol. 7, Issue 5, May 5, 2006, pp. 721-728, Article first published online: Mar. 27, 2006 DOI:10.1002/cbic.200600011.
R. Colin Hughes; "Galectins in kidney development", Glycoconjugate Journal 2004, vol. 19, Nos. 7-9, pp. 621-629; Publication date: Jan. 1, 2002; DOI: 10.1023/B:GLYC.0000014094.39168.fd.
Nathalie Bidon-Wagner, et al; "Human galectin-8 isoforms and cancer", Glycoconjugate Journal 2004, vol. 19, No. 7-9, pp. 557-563: Publication date Jan. 1, 2002; DOI:10.1023B:GLYC.0000014086.38343.98.
Ken Scott, et al; "Galectin-1: A bifunctional regulator of cellular proliferation", Glycoconjugate Journal 2004, vol. 19, Nos. 7-9, pp. 467-477; Publication date: Jan. 1, 2002; DOI: 10.1023/B:Glyc.0000014076.43288.89.
Anna R. Young, et al; "Galectins in parasite infection and allergic inflammation", Glycoconjugate Journal 2004, vol. 19, Nos. 7-9, pp. 601-606; Publication date: Jan. 1, 2002: DOI:10.1023/B:GLYC.0000014091.00844.0a.
Josiah Ochieng, et al; "Extracellular functions of galectin-3", Glycoconjugatge Journal 2004, vol. 19, Nos. 7-9, pp. 527-535; Publication date: Jan. 1, 2002; DOI: 10.1023/B:GLYC.0000014082.99675.2f.

(Continued)

Primary Examiner — Layla Bland
(74) Attorney, Agent, or Firm — Ladas & Parry LLP

(57) ABSTRACT

Novel synthesis routes for preparation of thiodigalactosides and intermediates are presented. The method includes the use of a 3-azido-galactosyl thiouronium salt derivative, which is activated to the corresponding thiol in situ, which in turn is directly reacted with a 3-azido-galactosyl bromide resulting in the 3,3'-di-azido-thio-di-galactoside before the thiol has a chance to reduce the azido 10 group. Hence, in situ formation of the 3-azido-galactosyl thiol from the thiouronium salt is essential in the synthesis procedure, because any other method that generate the thiol separately results in extensive unwanted azide reduction.

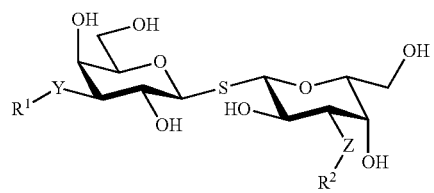

22 Claims, 1 Drawing Sheet

(56) References Cited

OTHER PUBLICATIONS

Antoninio Grassadonia, et al "90K (Mac-2 BP) and galectins in tumor progression and metastasis", Glycoconjugate Journal 2004, vol. 19, Nos. 7-9, pp. 551-556; Publication date Jan. 1, 2002; DOI: 10.1023/B:GLYC.0000014085.00706.d4.
Gabriel A. Rabinovich, et al, "Shedding light on the immunomodulatory properties of galectins: Novel regulators of innate and adaptive immune responses", Glycoconjugate Journal 2004, vol. 19, Nos. 7-9, pp. 565-573; Publication date Jan. 1, 2002; DOI: 10.1023/B:GLYC.0000014085.00706.d4.
Karen E. Pace, et al; "Insect galectins:Roles in immunity and development", Glyconconjugate Journal 2004, vol. 19, Nos. 7-9, pp. 607-614; Publication date: Jan. 1, 2002; DOI: 10.1023/B:GLYC.0000014092.86763.2f.
Ronald J. Patterson, et al; "Understanding the biochemical activities of galectin-1 and galectin-3 in the nucleus", Glycoconjugate Journal 2004, vol. 19, Nos. 7-9, pp. 499-506; Publication date: Jan. 1, 2002; DOI: 10.1023/B:GLYC.0000014079.87862.c7.
Jenny Almkvist, et al; "Galectins as inflammatory mediators", Glycoconjugate Journal 2004, vol. 19, Nos. 7-9, pp. 575-581; Publication date: Jan. 1, 2002; DOI: 10.1023/B:GLYC.0000014088.21242.e0.
Hidenori Horie, et al; "Galectin-1 plays essential roles in adult mammalian nervous tissues. Roles of oxidized galectin-1", Glycoconjugate Journal 2004, vol. 19, Nos. 7-9, pp. 479-489; Publication date Jan. 1, 2002; DOI: 10.1023/B:GLYC.0000014077.84016.52.
Mitsuomi Hirashima, et al; "Galectin-9 in physiological and pathological conditions", Glycoconjugate Journal 2004, vol. 19, Nos. 7-9, pp. 593-600; Publication date: Jan. 1, 2002; DOI: 10.1023/B:GLYC.0000014090.63206.2f.
Michael S. Lipkowitz, et al; "Galectin 9 is the sugar-regulated urate transporter/channel UAT", Glycoconjugate Journal 2004, vol. 19, Nos. 7-9, pp. 491-498; Publication date Jan. 1, 2002; DOI: 10.1023/B:GLYC.0000014078.65610.2f.
Daniel K. Hsu, et al; "Regulation of cellular homeostasis by galectins", Glycoconjugate Journal 2004, vol. 19, Nos. 7-9, pp. 507-515; Publication date Jan. 1, 2002; DOI: 10.1023/B:GLYC.0000014080.95829.52.
Josiah Ochieng, et al; "Extracellular functions of galectin-3", Glycoconjugate Journal 2004, vol. 19, Nos. 7-9, pp. 527-535; Publication date: Jan. 1, 2002; DOI: 10.1023/B:GLYC.0000014082.99675.2f.
Lorenzo Chiariotti, et al; "Galectin genes: Regulation of expression", Glycoconjugate Journal 2004, vol. 19, Nos. 7-9, pp. 441-449; Publication date Jan. 1, 2002; DOI: 10.1023/B:GLYC.0000014073.23096.3a.
Yehiel Zick, et al; "Role of galectin-8 as a modulator of cell adhesion and cell growth", Glycoconjugate Journal 2004, vol. 19, Nos. 7-9, pp. 517-526; Publication date Jan. 1, 2002; DOI: 10.1023/B:GLYC.0000014081.55445.af.
C. Fred Brewer; "Thermodynamic binding studies of galectin-1, -3 and -7", Glycoconjugate Journal 2004, vol. 19, Nos. 7-9; pp. 459-465; Publication date: Jan. 1, 2002; DOI: 10.1023/B:GLYC.0000014075.62724.d0.
Yukinori Takenaka, et al; "Galectin-3 and metastasis", Glycoconjugate Journal 2004, vol. 19, Nos. 7-9, pp. 543-549; Publication date: Jan. 1, 2002; DOI: 10.1023/B:GLYC.0000014084.01324.15.
International Preliminary Report on Patentability of PCT Appln. PCT/SE2009/050560.
George A. Patani, et al; "Bioisosterism: A Rational Approach in Drug Design"; Chemical Review 96 (8), pp. 3147-3176, May 15, 1996, p. 3172: Halogen bioisosteres, figures 84,85, table 51 and 52.
Ulf Ellervik, et al; "2-Bromoethyl glycosides for synthesis of glycoconjugates on solid support", Tetrahedron 61 (9), Sep. 24, 2004, pp. 2421-2429, scheme 6.
Ian Cumpstey, et al; "Double Affinity Amplification of Galectin-Ligand Interactions through Arginine-Arene Interactions: Synthetic, Thermodynamic, and Computational Studies with Aromatic Diamido Thiodigalactosides", Chemistry (Weinheim an der Bergstrasse, Germany), 14 (14), pp. 4233-4245, For claims 1-15: Schemes 3 and 4, for claim 31: Scheme 2, 2008.
Ian Cumpstey, et al; "$C_2$ -Symmetrical Thiodigalactoside Bis-Benzamido Derivatives as High-Affinity Inhibitors of Galectin-3: Efficient Lectin Inhibition through Double Arginine-Arene Interactions", Angewandte Chemie-International Edition 44 (32) 2005, pp. 5110-5112, Figure 1, Table 1: compounds 4A-4D.
Nigel M. Allanson, et al; "Synthesis of Phenyl 1-Thioglycopyranosiduronic Acids using a Sonicated Jones Oxidation", Tetrahedron Letters 39 (14), Nov. 25, 1997, pp. 1889-1892, table 2: entry 10.
Reynald Chevalier, et al; "Synthetic yeast oligomannosides as biological probes α-D-Man$p$(1→3) α-D-Man$p$(1→2) α-D-Man$p$(1→2) α-D-Man$p$as Crohn's disease markers", Tetrahedron 61 (32), Jan. 13, 2005, pp. 7669-7677, scheme 1: compound of formula 3.
Jonathan J. Gridley, et al; "Regioselective Lipase-catalysed acylation of 4, 6-O-bezylidene- α-and- β-D-pyranoside derivatives displaying a range of anomeric substituents", Tetrahedron 54 (49), Jul. 17, 1998, pp. 14925-14946, p. 14929: compound 12, p. 14931: compound 32.
Frederick P. Schwarz, et al "Thermodynamics of Bovine Spleen Galectin-1 Binding to Disaccharides: Correlation with Structuve and Its Effect on Oligomerization at the Denaturation Temperature", Biochemistry 1998, vol. 37, s. 5867-5877, the last compound in tables 1-4, figure 3.
Ian Cumpstey, et al; "Double Affinity Amplification of Galectin-Ligand Interactions through Arginine-Arene Interactions: Synthetic, Thermodynamic, and Computational Studies with Aromatic Diamido Thiodigalactosides", Chem. Eur. J. vol. 14, pp. 4233-4245; Mar. 2008.
El Sayed H. El Ashry, et al; "Synthesis of Interglycosidically S-Linked 1-Thio-Oligasoccharides Under Microwave Irradiation", Journal of Carbohydrate Chemistry: vol. 24, pp. 745-753; Published online Aug. 20, 2006.
Theodora W. Greene, et al; "Protective Groups in Organic Synthesis, Third Edition", Published Online: Apr. 23, 2002; 3 pages John Wiley & Sons, Inc.; Print ISBN: 9780471160199; Online ISBN: 9780471220572; DOI: 10.1002/0471220574.
Tomas Hudlisky, et al; "Chemoenzymatic Synthesis of D-*erythro*-$C_{18}$ - and L0threo-$C_{18}$ -Sphingosines", J. Org. Chem. vol. 59, pp. 7944-7946; Dec. 1994.
Richard C. Larock; Comprehensive Organic Transformations, A Guide to Functional Group Preperations, Two Volume Set, $2^{nd}$ Edition:, 2 pages; Dec. 2010; Wiley and Sons.
Monique Van Scherpenzeel, et al; "Synthesis and Evaluation of New Thiodigalactoside-Based Chemical Probes to Label Galectin-3",ChemBioChem, vol. 10, pp. 1724-1733, Jul. 6, 2009.

\* cited by examiner

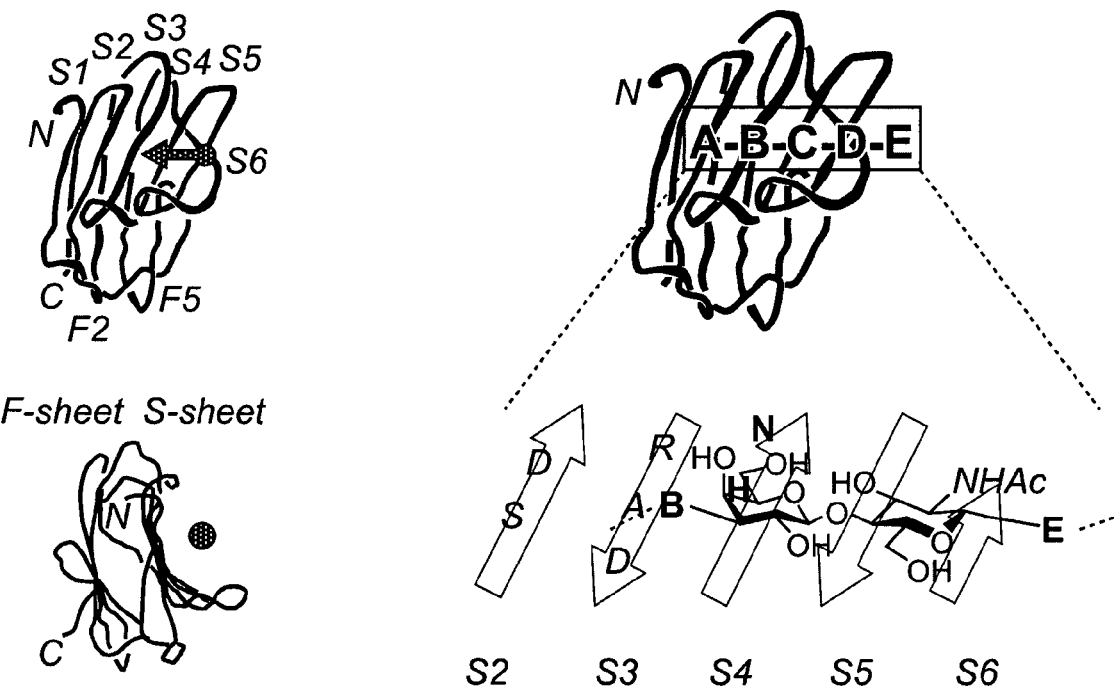

SYNTHESIS OF GALACTOSIDE INHIBITORS

TECHNICAL FIELD OF THE INVENTION

The present invention relates to a novel synthesis route for the manufacture of galactoside inhibitors, as well as new intermediates.

BACKGROUND ART

Galectins are proteins with a characteristic carbohydrate recognition domain (CRD) (Leffler et al., 2004) (FIG. 1). This is a tightly folded β-sandwich of about 130 aa (about 15 kDa) with the two defining features 1) a β-galactose binding site (C in FIG. 1) sufficient similarity in a sequence motif of about seven amino acids, most of which (about six residues) make up the β-galactose binding site. However, adjacent sites (A, B, D, E in FIG. 1) are required for tight binding of natural saccharides and different preferences of these give galectins different fine specificity for natural saccharides.

The recent completion of the human, mouse and rat genome sequences reveal about 15 galectins and galectin-like proteins in one mammalian genome with slight variation between species (Leffler et al., 2004).

Galectin subunits can contain either one or two CRDs within a single peptide chain. The first category, mono-CRDs galectins, can occur as monomers or dimers (two types) in vertebrates. The by far best studied galectins are the dimeric galectin-1, and galectin-3 that is a monomer in solution but may aggregate and become multimeric upon encounter with ligands (Leffler et al., 2004). These were the first discovered galectins and are abundant in many tissues. However, our recent phylogenetic analysis suggest that galectins with two CRDs within a peptide chain, bi-CRD galectins, appear to be more ancient and more central to the family than previously thought and that most of mammalian mono-CRD galectins may have descended from one or the other CRD of a bi-CRD galectin.

Potential Therapeutic Use of Galectin-3 Inhibitors.

Galectin-3 has been implicated in diverse phenomena and, hence, inhibitors may have multiple uses. It is easy to perceive this as a lack of specificity or lack of scientific focus. Therefore, the analogy with aspirin and the cyclooxygenases (COX-I and II) is useful. The COXs produce the precursor of a wide variety of prostaglandins and, hence, are involved in a diverse array of biological mechanisms. Their inhibitors, aspirin and other NSAIDs (non-steroid anti-inflammatory drugs), also have broad and diverse effects. Despite this, these inhibitors are very useful medically, and they have several different specific utilities.

So if galectins, like COXs, are part of some basic biological regulatory mechanism (as yet unknown), they are likely to be 'used by nature' for different purpose in different contexts. Galectin inhibitors, like NSAIDs, are not expected to wipe out the whole system, but to tilt the balance a bit.

Inhibition of Inflammation.

A pro-inflammatory role of galectin-3 is indicated by its induction in cells at inflammatory sites, a variety of effects on immune cells (e.g. oxidative burst in neutrophils, chemotaxis in monocytes), and decrease of the inflammatory response, mainly in neutrophils and macrophages, in null mutant mice (chapters by Rabinovich et al., Sato et al., and Almkvist et al. in Leffler (editor), 2004b). Moreover, knock-out mice of Mac-2BP, a galectin-3 ligand, have increased inflammatory response. Inflammation is a protective response of the body to invading organisms and tissue injury. However, if unbalanced, frequently it is also destructive and occurs as part of the pathology in many diseases. Because of this, there is great medical interest in pharmacological modulation of inflammation. A galectin-3 inhibitor is expected to provide an important addition to the arsenal available for this.

Treatment of Septic Shock.

The idea of a possible role of galectin-3 in septic shock comes from our own studies. Briefly, the argument goes as follows. It is known that septic shock involves dissemination of bacterial lipopolysaccharide into the blood stream, and that the pathological effects of this are mediated via neutrophil leukocytes. LPS does not activate the tissue-damaging response of the neutrophil. Instead, it primes the neutrophil, so that it is converted from unresponsive to responsive to other, presumably endogenous, activators. In septic shock, this priming happens prematurely in the blood stream. Endogenous activators could then induce the tissue damaging response in the wrong place and time. Several candidates have been proposed as these endogenous activators, including TNF-alfa. Inhibitors of these have been used in treatment schemes without much success. Since our own studies indicate that galectin-3 is a good candidate for being an endogenous activator of primed neutrophils (Almkvist et al. in Leffler (editor), 2004b), galectin-3 inhibitors may be very useful in septic shock.

Treatment of Cancer.

A large number of immunohistochemical studies show changed expression of certain galectins in cancer (van den Brule et. al. and Bidon et al. in Leffler (editor), 2004b) Galectin-3 is now an established histochemical marker of thyroid cancer, and neoexpression of galectin-4 is a promising marker of early breast cancer. The direct evidence for a role of galectin-3 in cancer comes from mouse models, mainly by Raz et al, but also others (Takenaka et al. in Leffler (editor), 2004b). In paired tumor cell lines (with decreased or increased expression of galectin-3), the induction of galectin-3 gives more tumors and metastasis and suppression of galectin-3 gives less tumors and metastasis. Galectin-3 has been proposed to enhance tumor growth by being anti-apoptotic, promote angiogenesis, or to promote metastasis by affecting cell adhesion. From the above it is clear that inhibitors of galectin-3 might have valuable anti-cancer effects. Indeed, saccharides claimed but not proven to inhibit galectin-3 have been reported to have anti-cancer effects. In our own study a fragment of galectin-3 containing the CRD inhibited breast cancer in a mouse model by acting as a dominant negative inhibitor (John et al., 2003).

Also galectin-1 is frequently over-expressed in low differentiated cancer cells, and galectin-9 or its relatives galectin-4 and galectin-8 may be induced in specific cancer types (Leffler (editor), 2004b). Galectin-1 induces apoptosis in activated T-cells and has a remarkable immunosuppressive effect on autoimmune disease in vivo (Rabinovich et al; and Pace et al. in Leffler (editor), 2004b). Therefore, the over-expression of these galectins in cancers might help the tumor to defend itself against the T-cell response raised by the host.

Null mutant mice for galectins-1 and -3 have been established many years ago. These are healthy and reproduce apparently normally in animal house conditions. However recent studies have revealed subtle phenotypes in function of neutrophils and macrophages (as described above) and in bone formation for galectin-3 null mutants, and in nerve and muscle cell regeneration/differentiation for the galectin-1 null mutants (Leffler et al., 2004; Watt in Leffler (editor), 2004b). Recently galectin-7 and galectin-9 null mutant mice have been generated and are also grossly healthy in animal house conditions, but have not yet been analysed in detail. The differences in site of expression, specificity and other properties make it unlikely that different galectins can replace each other functionally. The observations in the null mutant mice would indicate that galectins are not essential for basic life supporting functions as can be observed in normal animal house conditions. Instead they may be optimizers of normal function and/or essential in stress conditions not found in animal house conditions. The lack of strong effect in null mutant mice may make galectin inhibitors more favorable as drugs. If galectin activity contributes to pathological conditions as suggested above but less to normal conditions, then inhibition of them will have less unwanted side effects.
Known Inhibitors
Natural Ligands.

Solid phase binding assays and inhibition assays have identified a number of saccharides and glycoconjugates with the ability to bind galectins (Leffler et al., 2004). All galectins bind lactose with a $K_d$ of 0.5-1 mM. The affinity of D-galactose is 50-100 times lower. N-Acetyllactosamine and related disaccharides bind about as well as lactose, but for certain galectins, they can bind either worse or up to 10 times better. The best small saccharide ligands for galectin-3 were those carrying blood group A-determinants attached to lactose or lacNAc-residues and were found to bind up to about 50 times better than lactose. Galectin-1 shows no preference for these saccharides.

Larger saccharides of the polylactosamine type have been proposed as preferred ligands for galectins. In solution, using polylactosamine-carrying glycopeptides, there was evidence for this for galectin-3, but not galectin-1.

The above-described natural saccharides that have been identified as galectin-3 ligands are not suitable for use as active components in pharmaceutical compositions, because they are susceptible to acidic hydrolysis in the stomach and to enzymatic degradation. In addition, natural saccharides are hydrophilic in nature, and are not readily absorbed from the gastrointestinal tract following oral administration.
Synthetic Inhibitors (Pieters, 2006).

Saccharides coupled to amino acids with anti-cancer activity were first identified as natural compounds in serum, but subsequently, synthetic analogues have been made. Among them, those with lactose or Gal coupled to the amino acid inhibit galectins, but only with about the same potency as the corresponding underivatized sugar. A chemically modified form of citrus pectin that inhibits galectin-3 shows anti-tumor activity in vivo.

A divalent form of a lactosyl-amino acid had higher potency in a solid phase assay and clusters having up to four lactose moieties showed a strong multivalency effect when binding to galectin-3, but not to galectin-1 and -5. Cyclodextrin-based glycoclusters with seven galactose, lactose, or N-acetyllactosamine residues also showed a strong multivalency effect against galectin-3, but less so against galectins-1 and -7. Starburst dendrimers and glycopolymers, made polyvalent in lactose-residues, have been described as galectin-3 inhibitors with marginally improved potency as compared to lactose. The aforementioned synthetic compounds that have been identified as galectin-3 ligands are not suitable for use as active components in pharmaceutical compositions, because they are hydrophilic in nature and are not readily absorbed from the gastrointestinal tract following oral administration.

Natural oligosaccharides, glycoclusters, glycodendrimers, and glycopolymers described above are too polar and too large to be absorbed and in some cases are large enough to produce immune responses in patients. Furthermore, they are susceptible to acidic hydrolysis in the stomach and to enzymatic hydrolysis. Thus, there is a need for small synthetic molecules Thiodigalactoside is known to be a synthetic and hydrolytically stable, yet polar inhibitor, approximately as efficient as N-acetyllactosamine. A library of pentapeptides provided inhibitors against galectin-1 and -3, but only with low affinities, similar to that of galactose. Furthermore, peptides are not ideal agents for targeting galectins in vivo, as they are susceptible to hydrolysis and are typically polar. N-Acetyllactosamine derivatives carrying aromatic amides or substituted benzyl ethers at C-3" have been demonstrated to be highly efficient inhibitors of galectin-3, with unprecedented $IC_{50}$ values as low as 320 nM, which is a 20-fold improvement in comparison with the natural N-acetyllactosamine disaccharide (Sörme et al., 2005). These derivatives are less polar overall, due to the presence of the aromatic amido moieties and are thus more suitable as agents for the inhibition of galectins in vivo. However, said 3"-amido-derivatised compounds are still susceptible to hydrolytic degradation in vivo, due to the presence of a glycosidic bond in the N-acetyllactosamine disaccharide moiety and, although they are the best reported small molecule inhibitors of galectin-3, even further improved affinity is desirable.

WO 2005/113568 discloses a group of di-galactosides that have the general formula (I):

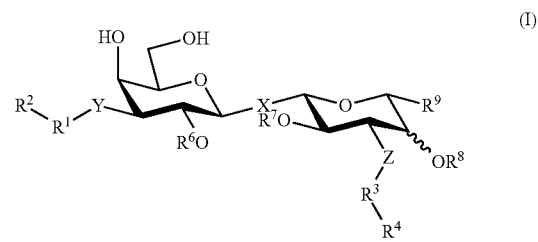

wherein
the configuration of one of the pyranose rings is β-D-galacto;
X is selected from the group consisting of O, S, SO, $SO_2$, NH, $CH_2$, and $NR^5$,
Y is selected from the group consisting of O, S, NH, $CH_2$, and $NR^5$, or is a bond;
Z is selected from the group consisting of O, S, NH, $CH_2$, and $NR^5$, or is a bond;
$R^1$ and $R^3$ are independently selected from the group consisting of CO, $SO_2$, SO, $PO_2$, PO, and $CH_2$ or is a bond;
$R^2$ and $R^4$ are independently selected from the group consisting of:
a) an alkyl group of at least 4 carbons, an alkenyl group of at least 4 carbons, an alkyl group of at least 4 carbons substituted with a carboxy group, an alkenyl group of at least 4 carbons substituted with a carboxy group, an alkyl group of at least 4 carbons substituted with an amino group, an alkenyl group of at least 4 carbons substituted with an amino group, an alkyl group of at least 4 carbons substituted with both an amino and a carboxy group, an alkenyl group of at least 4 carbons substituted with both an amino and a carboxy group, and an alkyl group substituted with one or more halogens;
b) a phenyl group substituted with at least one carboxy group, a phenyl group substituted with at least one halogen, a phenyl group substituted with at least one alkoxy group, a phenyl group substituted with at least one nitro group, a phenyl group substituted with at least one sulfo group, a phenyl group substituted with at least one amino group, a phenyl group substituted with at least one alkylamino group, a phenyl group substituted with at least one dialkylamino group, a phenyl group substituted with at least one hydroxy group, a phenyl group substituted with at least one carbonyl group and a phenyl group substituted with at least one substituted carbonyl group, c) a naphthyl group, a naphthyl group substituted with at least one carboxy group, a naphthyl group substituted with at least one halogen, a naphthyl group substituted with at least one alkoxy group, a naphthyl group substituted with at least one nitro group, a naphthyl group substituted with at least one sulfo group, a naphthyl group substituted with at least one amino group, a naphthyl group substituted with at least one alkylamino group, a naphthyl group substituted with at least one dialkylamino group, a naphthyl group substituted with at least one hydroxy group, a naphthyl group substituted with at least one carbonyl group and a naphthyl group substituted with at least one substituted carbonyl group; and d) a heteroaryl group, a heteroaryl group substituted with at least one carboxy group, a heteroaryl group substituted with at least one halogen, a heteroaryl group substituted with at least one alkoxy group, a heteroaryl group substituted with at least one nitro group, a heteroaryl group substituted with at least one sulfo group, a heteroaryl group substituted with at least one amino group, a heteroaryl group substituted with at least one alkylamino group, a heteroaryl group substituted with at least one dialkylamino group, a heteroaryl group substituted with at least one hydroxy group, a heteroaryl group substituted with at least one carbonyl group and a heteroaryl group substituted with at least one substituted carbonyl group.

$R^5$ is selected from the group consisting of hydrogen, an alkyl group, an alkenyl group, an aryl group, a heteroaryl group, and a heterocycle.

$R^6$ and $R^8$ are independently selected from the group consisting of a hydrogen, an acyl group, an alkyl group, a benzyl group, and a saccharide.

$R^7$ is selected from the group consisting of a hydrogen, an acyl group, an alkyl group, and a benzyl group.

$R^9$ is selected from the group consisting of a hydrogen, a methyl group. hydroxymethyl group, an acyloxymethyl group, an alkoxymethyl group, and a benzyloxymethyl group.

Specific embodiments of the invention according to WO 2005/113568 are indicated in claims 3-19 of WO 2005/113568.

The synthesis route disclosed therein is however, complicated and will not provide the best yields desired for the manufacture of larger quantities. Said synthesis of the thiodigalactoside inhibitors in accordance with prior art followed methods well known to one skilled in the art and are explained in detail in WO 2005/113568 in the passage "Synthesis of thiodigalactosides" on pages 22-23. The synthesis of WO 2005/113568 diverges after the first step (see 1 in scheme 1 of WO 2005/113568) and for each individual inhibitor synthesized five separate reactions are required; azide reduction, acylation, bromination, sulfide reaction, and O-acetyl removal.

WO 2005/113568 gives several specific examples of preparation of di-galactosides:
2,4,6-tri-O-acetyl-3-deoxy-3-(3,5-dimethoxybenzamido)-α-D-galactopyranosyl bromide—see preparation 9 on pages 27-28 of WO 2005/113568,
bis-(2,4,6-tri-O-acetyl-3-deoxy-3-(3,5-dimethoxybenzamido)-β-D-galactopyranosyl)sulfane—see preparation 14 on page 28 of WO 2005/113568,
bis-[3-deoxy-(3,5-dimethoxybenzamido)-β-D-galactopyranosyl]sulfane—see preparation 19 on pages 28-29 of WO 2005/113568, WO 2005/113569 discloses a group of galactosides that have the general formula denoted II in WO 2005/113569:

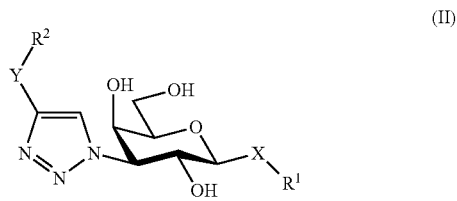

(II)

wherein
the configuration of the pyranose ring is D-galacto;
X is selected from the group consisting of O, S, NH, $CH_2$, and $NR^4$, or is a bond;
Y is selected from the group consisting of $CH_2$, CO, $SO_2$, SO, $PO_2$ and PO, phenyl, or is a bond;
$R^1$ is selected from the group consisting of;
a) a saccharide;
b) a substituted saccharide;
c) D-galactose;
d) substituted D-galactose;
e) C3-[1,2,3]-triazol-1-yl-substituted D-galactose;
f) hydrogen, an alkyl group, an alkenyl group, an aryl group, a heteroaryl group, and a heterocycle and derivatives thereof;
g) an amino group, a substituted amino group, an imino group, or a substituted imino group.
$R^2$ is selected from the group consisting of;
hydrogen, an amino group, a substituted amino group, an alkyl group, a substituted alkyl group, an alkenyl group, a substituted alkenyl group, an alkynyl group, a substituted alkynyl group, an alkoxy group, a substituted alkoxy group, an alkylamino group, a substituted alkylamino group, an arylamino group, a substituted arylamino group, an aryloxy group, a substituted aryloxy group, an aryl group, a substituted aryl group, a heteroaryl group, a substituted heteroaryl group, and a heterocycle, a substituted heterocycle.

Specific embodiments of the invention according to WO 2005/113569 are indicated in claim 9 of WO 2005/113569. In other specific embodiments are Y is a phenyl group or a carbonyl group. In yet other specific embodiments X is S or O and Y is a phenyl or a carbonyl group. Other specific embodiments are listed in claim 10 of WO 2005/113569.

In particular, thiodigalactoside derivatives, such as bis-(3-deoxy-3-(4-(methylaminocarbonyl)-1H-[1,2,3]-triazol-1-yl)-β-D-galactopyranosyl)sulfane and analogs thereof, are high-affinity galectin inhibitors. However, the synthesis route towards the thiodigalactoside derivative bis-(3-deoxy-3-(4-(methylaminocarbonyl)-1H-[1,2,3]-triazol-1-yl)-β-D-galactopyranosyl)sulfane disclosed therein is complicated and will not provide the best yields desired for the manufacture of larger quantities. Said synthesis of the thiodigalactoside inhibitors in accordance with prior art followed methods well known to one skilled in the art and are explained in detail in WO 2005/113569 in the passage "Synthesis of triazoles" on pages 20-22, with particular reference to scheme 4 illustrated on page 22. The known compound 1,2,4,6-tri-O-acetyl-3-azido-3-deoxy-D-galactopyranose, which preparation involves 11 steps all requiring chromatographic purification, was reacted with methyl propiolate under copper(I) catalysis to give the triazole. The triazole was converted by treatment with hydrogen bromide in glacial acetic acid into the glycosyl bromide, which was used directly in reaction with sodium sulfide to give the protected thiodigalactoside derivative. The O-acetyl protecting groups were removed via aminolysis afford the final thiodigalactosides. Alternatively, other alkynes could be reacted with 1,2,4,6-tri-O-acetyl-3-azido-3-deoxy-D-galactopyranose to provide triazole analogs. Hence, the synthesis diverges after the first step and for each individual inhibitor synthesized four separate reactions are required; cycloaddition with an alkyne, bromination, sulfide reaction, and aminolysis.

WO 2005/113569 gives several specific examples of preparation of di-galactosides:

1,2,4,6-Tetra-O-acetyl-3-deoxy-3-[4-(methoxycarbonyl)-1H-[1,2,3]-triazol-1-yl]-D-galactopyranose—see preparation 23 on pages 36-37 of WO 2005/113569, 2,4,6-Tri-O-acetyl-3-deoxy-3-[4-(methoxycarbonyl)-1H-1,2,3-triazol-1-yl]-α-D-galactopyranosyl bromide—see preparation 24 on page 37 of WO 2005/113569, bis-[2,4,6-tri-O-acetyl-3-deoxy-3-(4-(methoxycarbonyl)-1H-1,2,3-triazol-1-yl)-β-D-galactopyranosyl]sulfane—see preparation 25 on pages 36-37 of WO 2005/113569, bis-(3-deoxy-3-{4-[(methylamino)carbonyl]-1H-1,2,3-triazol-1-yl}-β-D-galactopyranosyl)sulfane—see preparation 26 on page 38 of WO 2005/113569,

BRIEF DESCRIPTION OF THE DRAWING

FIG. 1 illustrates a galectins which is a protein with a characteristic carbohydrate recognition domain (CRD). This is a tightly folded β-sandwich of about 130 amino acids (about 15 kDa) with the two defining features 1) a β-galactose binding site (C in FIG. 1) sufficient similarity in a sequence motif of about seven amino acids, most of which (about six residues) make up the β-galactose binding site. However, adjacent sites (A, B, D, E) are required for tight binding of natural saccharides and different preferences of these give galectins different fine specificity for natural saccharides.

SUMMARY OF THE PRESENT INVENTION

The present invention relates to a novel synthesis method for preparation of thio-di-galactosides. One advantage of the present invention is that it provides a more efficient manufacture of thiodigalactosides compared to prior art methods.

The method comprises the use of a 3-azido-galactosyl thiouronium salt derivative, which is activated to the corresponding thiol in situ, which in turn is directly reacted with a 3-azido-galactosyl bromide resulting in the 3,3'-di-azido-thio-di-galactoside before the thiol has a chance to reduce the azido group. Hence, in situ formation of the 3-azido-galactosyl thiol from the thiouronium salt is essential in the synthesis procedure, because any other method that generate the thiol separately results in extensive unwanted azide reduction.

One aspect of the invention relates to a method for preparation of a 3,3'-di-azido-thio-digalactoside by reacting a compound of formula (8) with a compound of formula (9) to form an azido compound of formula (10):

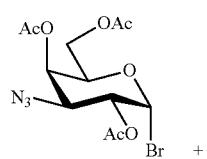

(8)

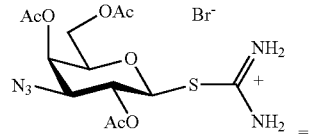

(9)

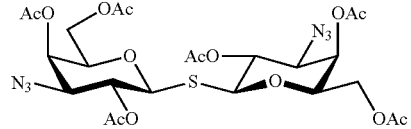

(10)

Another aspect of the invention relates to a method for preparing thio-di-galactosides of the general formula (12)

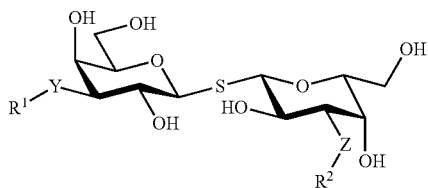

(12)

wherein
the configuration of one of the pyranose rings is β-D-galacto;
Y and Z are independently selected from being CONH or a 1H-1,2,3-triazole ring;
$R^1$ and $R^2$ are independently selected from the group consisting of:
a) an alkyl group of at least 4 carbons, an alkenyl group of at least 4 carbons, an alkynyl group of at least 4 carbons;
b) a carbamoyl group, a carbamoyl group substituted with an alkyl group, a carbamoyl group substituted with an alkenyl group, a carbamoyl group substituted with an alkynyl group, a carbamoyl group substituted with an aryl group, a carbamoyl group substituted with an substituted alkyl group, and a carbamoyl group substituted with an substituted aryl group;
c) a phenyl group substituted with at least one carboxy group, a phenyl group substituted with at least one halogen, a phenyl group substituted with at least one alkyl group, a phenyl group substituted with at least one alkoxy group, a phenyl group substituted with at least one trifluoromethyl group, a phenyl group substituted with at least one trifluoromethoxy group, a phenyl group substituted with at least one sulfo group, a phenyl group substituted with at least one hydroxy group, a phenyl group substituted with at least one carbonyl group, and a phenyl group substituted with at least one substituted carbonyl group;
d) a naphthyl group, a naphthyl group substituted with at least one carboxy group, a naphthyl group substituted with at least one halogen, a naphthyl group substituted with at least one alkyl group, a naphthyl group substituted with at least one alkoxy group, a naphthyl group substituted with at least one sulfo group, a naphthyl group substituted with at least one hydroxy group, a naphthyl group substituted with at least one carbonyl group, and a naphthyl group substituted with at least one substituted carbonyl group;

e) a heteroaryl group, a heteroaryl group substituted with at least one carboxy group, a heteroaryl group substituted with at least one halogen, a heteroaryl group substituted with at least one alkoxy group, a heteroaryl group substituted with at least one sulfo group, a heteroaryl group substituted with at least one arylamino group, a heteroaryl group substituted with at least one hydroxy group, a heteroaryl group substituted with at least one halogen, a heteroaryl group substituted with at least one carbonyl group, and a heteroaryl group substituted with at least one substituted carbonyl group; and f) a thienyl group, a thienyl group substituted with at least one carboxy group, a thienyl group substituted with at least one halogen, a thienyl thienyl group substituted with at least one alkoxy group, a thienyl group substituted with at least one sulfo group, a thienyl group substituted with at least one arylamino group, a thienyl group substituted with at least one hydroxy group, a thienyl group substituted with at least one halogen, a thienyl group substituted with at least one carbonyl group, and a thienyl group substituted with at least one substituted carbonyl group.

One embodiment of the invention provides a method for the preparation of thio-di-galactosides of the general formula (13)

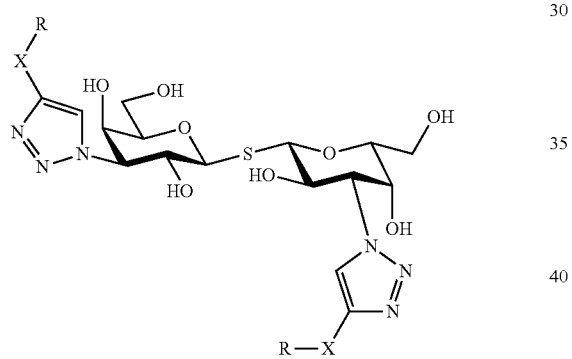

(13)

wherein the configuration of at least one of the pyranose rings is D-galacto;

X is selected from the group consisting of $CH_2$, CO, $SO_2$, SO, $PO_2$, PO, phenyl, an aryl group, a substituted aryl group, and a bond; and R is selected from the group consisting of: hydrogen, an amino group, a substituted amino group, an alkyl group, a substituted alkyl group, an alkenyl group, a substituted alkenyl group, an alkynyl group, a substituted alkynyl group, an alkoxy group, a substituted alkoxy group, an alkylamino group, a substituted alkylamino group, an arylamino group, a substituted arylamino group, an aryloxy group, a substituted aryloxy group, an aryl group, a substituted aryl group, a heteroaryl group, a substituted heteroaryl group, and a heterocycle, a substituted heterocycle.

DETAILED DESCRIPTION OF THE PRESENT INVENTION

The novel route of synthesis is clearly shown in scheme 1 below, and relates in particular to the reaction of compounds of formulae (8) and (9) in the final step to form a compound of formula (10), which thiodigalactoside compound is further deprotected to form compound of formula (11) and then further reacted to form the compounds of formula (12) or (13).

Scheme 1:

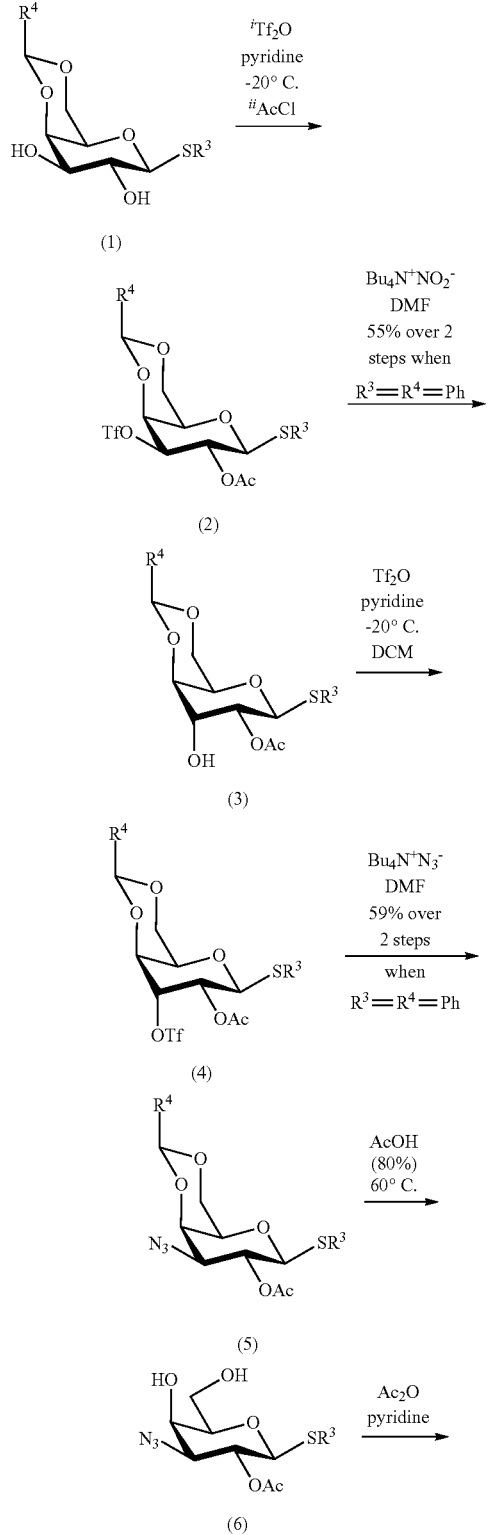

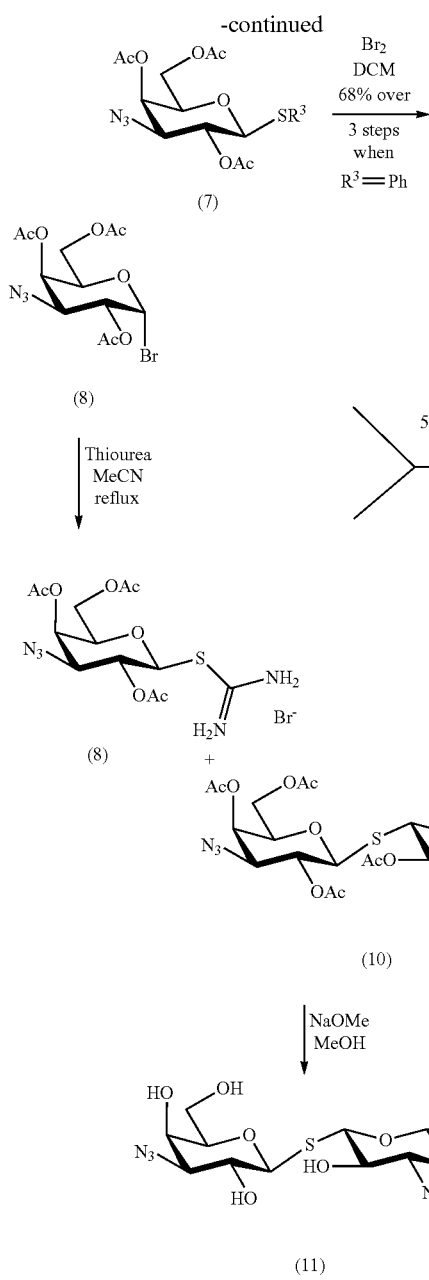

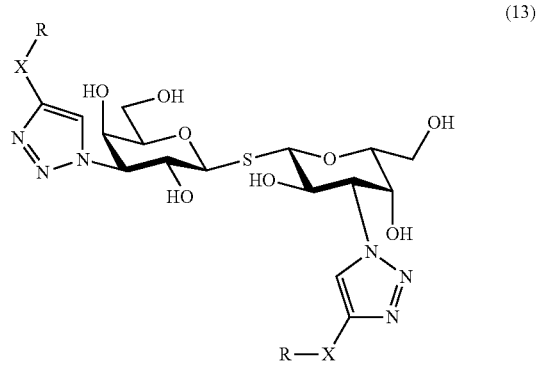

The deprotection is performed by means known per se: Treatment of compound (10) with methanolic sodium methoxide gives compound (11)....

Also the further reaction is performed using methods and synthesis steps known per se: Reduction of (11) followed by acylation give amido compounds (12) and reaction of compound (11) with terminal acetylenes in the presence of Cu(I) gives triazole compounds (13)....

Further, the invention relates to certain new thio-di-galactosides of formula (13):

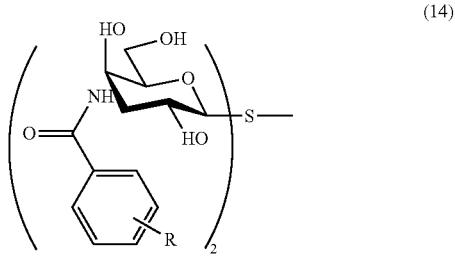

wherein
- the configuration of at least one of the pyranose rings is D-galacto;
- X is a bond
- R is a phenyl group, which is substituted in any position with one or more substituents selected from the group consisting of methyl, ethyl, isopropyl, tert-butyl, fluoro, chloro, bromo and trifluormethyl, and/or of formula (14)

(14)

wherein R is one or more trifluoromethyl, preferably in meta and/or para position.

In the present disclosure, the term "alkyl group" is meant to comprise from 1 to 12 carbon atoms. Said alkyl group may be straight- or branched-chain. Said alkyl group may also form a cycle comprising from 3 to 12 carbon atoms.

In the present disclosure, the term "alkenyl group" is meant to comprise from 2 to 12 carbon atoms. Said alkenyl group comprises at least one double bond.

In the present disclosure the term "aryl group" is meant to comprise from 4 to 18 carbon atoms. Said aryl group may be a phenyl group or a naphthyl group.

In the present disclosure, the term "alkoxy group" is meant to comprise from 1 to 12 carbon atoms. Said alkoxy group may be a methoxy group or an ethoxy group.

In the present disclosure, the term "alkylamino group" is meant to comprise from 1 to 12 carbon atoms.

In a further aspect of the invention it relates to intermediates as well, in particular the intermediates of the compounds (2) to (7) and (9) above.

The phenyl group present on the acetal carbon may be substituted with a methyl, methoxy, alkyl, alkoxy, or aryl or fused with an aryl group as well.

The phenyl group present on the S-atom, the thio group, may be substituted with a methyl, methoxy, alkyl, alkoxy, halo, nitro, or amido group as well.

In addition to acetates, the esters of compounds (2) to (10) may be aliphatic esters of 1 to 6 carbon atoms, aromatic esters, or substituted aromatic ester.

As explained above, the reaction of the invention illustrated in scheme 1 results in a thiodigalactoside compound of formula (10), which is further deprotected to form compound of formula (11) and then further reacted include substituents to form the desired final compound of formula (12) or the particular embodiment of formula (13).

In the present disclosure, the term "arylamino group" is meant to comprise from 4 to 12 carbon atoms. Said "arylamino group" may be aniline, carboxylated aniline or halogenated aniline.

In the present disclosure, the term "heteroaryl group" is meant to comprise from 4 to 18 carbon atoms, wherein at least one atom of the ring is a heteroatom, i.e. not a carbon. Preferably, said heteroatom is N, O or S. Said heteroaryl group may be a quinoline, isoquinoline pyridine, a pyrrole, a furan or a thiophene group.

In the present disclosure, the term "acyl group" is meant to be aliphatic or aromatic to comprise from 2 to 7 carbon atoms. Said acyl group may be a benzoyl, acetyl, naphthoyl, or a trimethylacetyl group.

In the present disclosure, the term "acyloxy group" is meant to be aliphatic or aromatic and to comprise from 2 to 7 carbon atoms. Said acyloxy group may be a benzoyloxy, acetoxy, naphthoyloxy, or a trimethylacetoxy group.

The above-mentioned groups may naturally be substituted with any other known substituents within the art of organic chemistry. The groups may also be substituted with two or more of the substituents. Examples of substituents are halogen, alkoxy having 1 to 4 carbon atoms, nitro, sulfo, amino, hydroxy, and carbonyl groups.

DETAILED EMBODIMENTS

Compound 1 is known in the literature. Compounds 3, 5, 7 are crystalline and can thus easily be purified.

The applicability of compound (11) in the synthesis of galectin inhibitors is exemplified below with the preparation of di-(3-deoxy-3-{4-[2-fluorophenyl]-1H-1,2,3-triazol-1-yl}-β-D-galactopyranosyl)sulfane (26) and di-(3-deoxy-3-{4-[2-trifluoromethyl-phenyl]-1H-1,2,3-triazol-1-yl}-β-D-galactopyranosyl)sulfane (27):

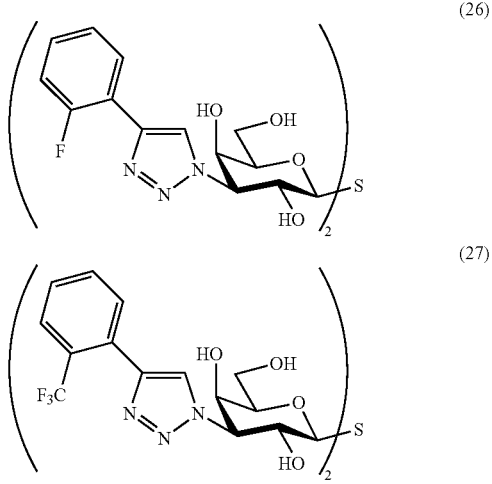

Experimental Section

Phenyl 2-O-acetyl-4,6-O-benzylidene-1-thio-3-O-trifluoromethane-sulfonyl-β-D-galactopyranoside (2)

Compound 1 (10.5 g, 29.2 mmol) was dissolved in dried pyridine (4.73 mL, 58.4 mmol) and dried CH$_2$Cl$_2$ (132 mL). The reaction mixture was cooled, under stirring, until −20° C. (Ice and NaCl bath 3:1). Slowly and under N$_2$ atmosphere, Tf$_2$O (5.68 mL, 33.6 mmol) was added. The reaction mixture was monitored by TLC (heptane:EtOAc, 1:1 and toluene:acetone, 10:1). When the reaction was complete, AcCl (2.29 mL, 32.1 mmol) was added and keeping stirring, the temperature was increased to room temperature. This mixture was monitored by TLC too (heptane:EtOAc, 1:1 and toluene:acetone, 10:1). When it was complete, it was quenched with CH$_2$Cl$_2$ and washed with 5% HCl, NaHCO$_3$ (sat) and NaCl (sat). The organic layer was dried over MgSO$_4$, filtered and concentrated under reduced pressure.

Phenyl 2-O-acetyl-4,6-O-benzyliden-1-thio-β-D-gulopyranoside (3)

Tetrabutylammonium nitrite (25.3 g, 87.7 mmol) was added to a solution of compound 2 (15.6 g, 29.2 mmol) in DMF (110 mL) and was kept stirring, under N$_2$ atmosphere, at 50° C. (The reaction started being purple and turned garnet). The reaction was monitored by TLC (heptane:EtOAc, 1:1 and toluene:acetone, 10:1) and quenched with CH$_2$Cl$_2$. The mixture was washed with 5% HCl, NaHCO$_3$ (sat) and NaCl (sat). The organic layer was dried over MgSO$_4$, filtered and concentrated under reduced pressure followed by purification by flash chromatography (Eluent heptane:EtOAc, 1:1 and heptane:EtOAc, 1:2) and recrystallized from a mixture of EtOAc and Heptane (1:3). $^1$H NMR in CDCl$_3$ δ7.60-7.57 (m, 2H, Ar), 7.43-7.40 (m, 2H, Ar), 7.37-7.34 (m, 3H, Ar), 7.29-7.25 (m, 3H, Ar), 5.50 (s, 1H, PhCH), 5.15 (d, 1H, J=10.29 Hz, H-1), 5.10 (dd, 1H, J=10.27 Hz, 2.85 Hz, H-2), 4.36 (dd, 1H, J=12.49 Hz, 1.4 Hz, H-6), 4.18 (br s, 1H, H-3), 4.08 (dd, 1H, J=3.59 Hz, 1.04 Hz, H-6), 4.03 (dd, 1H, J=12.53 Hz, 1.75 Hz, H-4), 3.88 (s, 2H, H-5+OH), 2.12 (s, 3H, OAc).

Phenyl 2-O-acetyl-4,6-O-benzylidene-1-thio-3-O-trifluoromethane-sulfonyl-β-D-gulopyranoside (4)

Compound 3 (1.00 g, 2.48 mmol) was dissolved in dried CH$_2$Cl$_2$ (12.5 mL) and dried pyridine (0.40 mL, 4.96 mmol). The reaction mixture was cooled, under stirring, until −20° C. (Ice and NaCl bath 3:1). Slowly and under N$_2$ atmosphere, Tf$_2$O (0.48 mL, 2.85 mmol) was added. The reaction mixture was monitored by TLC (heptane:EtOAc, 1:1 and toluene:acetone, 10:1) and when it was complete, it was quenched with CH$_2$Cl$_2$ and washed with 5% HCl, NaHCO$_3$ (sat) and NaCl (sat). The organic layer was dried over MgSO$_4$, filtered and concentrated under reduced pressure until being dry.

Phenyl 2-O-acetyl-3-azido-4,6-O-benzylidene-3-deoxy-1-thio-β-D-galactopyranoside (5)

Tetrabutylammonium azide (2.12 g, 7.44 mmol) was added carefully to a solution of compound 4 (1.3256 g, 2.48 mmol) in DMF (10 mL) and was kept stirring, under N$_2$ atmosphere, at 50° C. The reaction was monitored by TLC (E:H, 1:1) and concentrated under reduced pressure followed by purification by flash chromatography (Eluent heptane:EtOAc, 2:1 and heptane:EtOAc, 1:1). $^1$H NMR in CDCl$_3$ δ 7.61-7.58 (m, 2H, Ar), 7.44-7.41 (m, 2H, Ar), 7.39-7.36 (m, 3H, Ar), 7.30-7.24 (m, 3H, Ar), 5.59 (s, 1H, PhCH), 5.35 (t, 1H, J=9.95 Hz, H-2), 4.73 (d, 1H, J=9.63 Hz, H-1), 4.44 (dd, 1H, J=6.24 Hz, 1.60 Hz, H-6), 4.35-4.34 (dd, 1H, J=3.33 Hz, 0.88 Hz, H-4), 4.11 (dd, 1H, J=12.48 Hz, 1.67 Hz, H-6), 3.57 (d, 1H, J=1.15 Hz, H-5), 3.44 (dd, 1H, J=10.21 Hz, 3.29 Hz, H-3), 2.17 (s, 3H, OAc).

Phenyl 2-O-acetyl-3-azido-3-deoxy-1-thio-β-D-galactopyranoside (6)

Compound 5 (470 mg, 1.1 mmol) was dissolved in 80% acetic acid (75 mL) and the mixture was heated at 60° C. The reaction was monitored by TLC (heptane:EtOAc, 1:1). When the reaction was complete, the mixture was concentrated under reduced pressure and heating.

Phenyl 2,4,6-tri-O-acetyl-3-azido-3-deoxy-1-thio-β-D-galactopyranoside (7)

Acetic anhydride (30 mL) was added to a solution of compound 6 (373 mg, 1.1 mmol) in dry pyridine (30 mL). The reaction was monitored by TLC (heptane:EtOAc, 1:1) and when it was complete, it was concentrated under reduced pressure. $^1$H NMR in CDCl$_3$ δ 7.54-7.51 (m, 2H, Ar), 7.35-7.30 (m, 3H, Ar), 5.46 (dd, 1H, H-4), 5.23 (t, 1H, H-2), 4.73 (d, 1H, H-1), 4.15 (d, 2H, H-6, H-6), 3.94 (dt, 1H, H-5), 3.68 (dd, 1H, H-3), 2.18 (s, 3H, OAc), 2.15 (s, 3H, OAc), 2.06 (s, 3H, OAc).

2,4,6-tri-O-acetyl-3-azido-3-deoxy-α-D-galactopyranosyl bromide (8)

Compound 7 (237.4 mg, 560 µmol) was dissolved in dry CH$_2$Cl$_2$ (2 mL), and bromine (32 µl, 620 µmol) was added. The reaction was monitored by TLC (heptane:EtOAc, 1:1). When the reaction was complete, a small amount of cyclopentene was added to the reaction mixture to remove the rests of Br$_2$. The mixture was concentrated under reduced pressure and purified by quick Flash chromatography (Eluyent: 500 mL heptane:EtOAc, 2:1).

2,4,6-tri-O-acetyl-3-azido-3-deoxy-α-D-galactopyranose-1-isothiouronium bromide (9)

The sensitive bromide 8 (70.6 mg, 180 µmol) was immediately dissolved in dry acetonitrile (1.7 mL) and refluxed with thiourea (13.7 mg, 180 µmol) under N$_2$ for 4 hours. The reaction was monitored by TLC (heptane:EtOAc, 1:1) and when it was complete, the mixture was cooled.

Di-(2,4,6-tri-O-acetyl-3-azido-3-deoxy-β-D-galactopyranosyl)-sulfane (10)

The sensitive bromide 8 (77.0 mg, 196 µmol) and Et$_3$N (60 µl, 430 µmol) was added to the last mixture (9). The reaction was monitored by TLC (heptane:EtOAc, 1:1). When it was complete, the reaction mixture was concentrated under reduced pressure and without heating. The residue was purified by Flash chromatography (Eluyent: heptane:EtOAc, 1:1). $^1$H NMR in CDCl$_3$ δ 5.50 (dd, 2H, H-4), 5.23 (t, 2H, H-2, H-2'), 4.83 (d, 2H, H-1, H-1'), 4.15 (dd, 4H, H-6, H-6, H-6', H-6'), 3.89 (dt, 2H, H-5, H-5'), 3.70 (dd, 2H, H-3, H-3'), 2.19 (s, 6H, 2OAc), 2.15 (s, 6H, 2OAc), 2.18 (s, 6H, 2OAc).

Di-(3-azido-3-deoxy-β-D-galactopyranosyl)-sulfane (11)

Compound 10 (9 mg, 0.000014 mol) was dissolved in dry MeOH (240 µl) and dry CH$_2$Cl$_2$ (100 µl), and NaOMe (1.4 µl, 1.4 µmol) was added. The reaction was monitored by TLC (heptane:EtOAc 1:1 and D:M 5:1). When the reaction was complete, the mixture was neutralized with Duolite C436 until pH 7, filtered and washed with MeOH. The filtered solution was concentrated under reduced pressure. $^1$H NMR in CDCl$_3$ δ 4.72 (d, 2H, J=9.7 Hz, H-1, H-1'), 3.95 (br s, 2H, H-4, H-4'), 3.84 (t, 2H, J=9.8 Hz, H-2, H-2'), 3.74 (dd, 2H, J=11.47 Hz, 7.23 Hz, H-6, H-6'), 3.64 (dd, 2H, J=11.48 Hz, 4.72 Hz, H-6, H-6'), 3.60-3.55 (ddd, 2H, 7.15 Hz, 4.67 Hz, 0.93 Hz, H-5, H-5'), 3.36 (dd, 2H, J=10 Hz, 3.05 Hz, H-3, H-3').

The applicability of compound (11) in the synthesis of galectin inhibitors is exemplified below with the preparation of di-(3-deoxy-3-{4-[2-fluorophenyl]-1H-1,2,3-triazol-1-yl}-β-D-galactopyranosyl)sulfane (26) and di(3-deoxy-3-{4-[2-trifluoromethyl-phenyl]-1H-1,2,3-triazol-1-yl}-β-D-galactopyranosyl)sulfane (27):

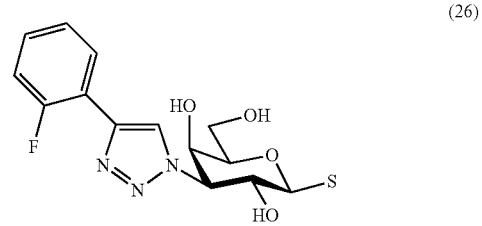

(26)

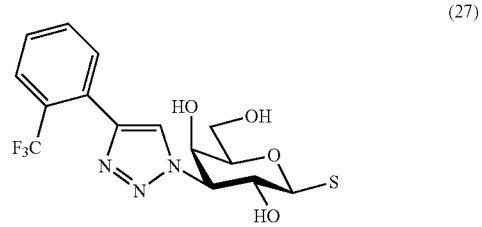

(27)

Di-(3-deoxy-3-{4-[2-fluorophenyl]-1H-1,2,3-triazol-1-yl}-β-D-galactopyranosyl)sulfane (26)

Compound (11) (12 mg, 0.030 mmol) was dissolved in DMF (3 mL) and 1-ethynyl-2-fluorobenzene (10.2 µL, 0.090 mmol), CuI (0.6 mg, 0.0030 mmol) and triethylamine (4.2 µL, 0.030 mmol) were added under N$_2$ atmosphere. The solution was kept stirring. The reaction was monitored by TLC (CH$_2$Cl$_2$:MeOH 5:1) and when complete, the mixture was concentrated under reduced pressure and purified by flash chromatography (CH$_2$Cl$_2$:MeOH 8:1), followed by RP_HPLC (C18, water:MeCN gradient with 0.1% trifluoroacetic acid). $^1$H NMR in CDCl$_3$ δ 8.5 (d, 2H, J=3.5 Hz, 2 triazole), 8.1 (dt, 2H, J=7.63 Hz, 1.77 Hz, Ar), 7.4-7.33 (m, 2H, Ar), 7.3-7.25 (dt, 2H, J=7.67 Hz, 1.22 Hz, Ar), 7.23-7.17 (m, 2H, Ar), 4.92 (dd, 2H, J=10.61, 2.92, H-3, H-3'), 4.89 (d, 2H, J=10 Hz, H-1, H-1'), 4.8 (br t, 2H, J=10 Hz, H-2, H-2'), 4.16 (d, 2H, J=2.86 Hz, H-4, H-4'), 3.91-3.84 (m, 4H, H-5, H-5', H, 6, H-6'), 3.76-3.69 (m, 2H, H-6, H-6').

Di-(3-deoxy-3-{4-[2-trifluoromethyl-phenyl]-1H-1,2,3-triazol-1-yl}-β-D-galactopyranosyl)sulfane (27)

Compound 11 (14.6 mg, 0.036 mmol) was dissolved in DMF (3.6 mL) and 1-ethynyl-2-trifluoromethylbenzene (15.0 µL, 0.108 mmol), CuI (0.7 mg, 0.0036 mmol) and triethylamine (5 µL, 0.036 mmol) were added under N$_2$ atmosphere. The solution was kept stirring. The reaction was monitored by TLC (CH$_2$Cl$_2$:MeOH 5:1) and when complete, the mixture was concentrated under reduced pressure and purified by flash chromatography (CH$_2$Cl$_2$:MeOH 8:1), followed by RP_HPLC (C18, water:MeCN gradient with 0.1% trifluoroacetic acid). $^1$H NMR in CDCl$_3$ δ 8.3 (s, 2H, 2 triazole), 7.83 (d, 2H, J=7.86 Hz, Ar), 7.76-7.67 (m, 4H, Ar), 7.59 (dt, 2H, J=7.56 Hz, 0.73 Hz, Ar), 4.92 (dd, 2H, J=10.7 Hz, 2.94 Hz, H-3, H-3'), 4.87 (d, 2H, J=10.1 Hz, H-1, H-1'), 4.71

(br t, 2H, J=10.1 Hz, H-2, H-2'), 4.13 (d, 2H, J=2.67 Hz, H-4, H-4'), 3.87 (dd, 2H, J=8 Hz, 3.75 Hz, H-5, H-5'), 3.82 (dd, 2H, J=11.10 Hz, 7.6, H-6, H-6'), 3.68 (dd, 2H, J=11.12, 3.85, H-6, H-6').

REFERENCES

John, C. M., Leffler, H., Kahl-Knutsson, B., Svensson, I., and Jarvis, G. A. (2003) Truncated Galectin-3 Inhibits Tumor Growth and Metastasis in Orthotopic Nude Mouse Model of Human Breast *Cancer. Clin. Cancer Res.* 9:2374-2383.

Leffler, H., Carlsson, S., Hedlund, M., Qian, Y. and Poirier, F. (2004) Introduction to galectins. *Glycoconj. J.* 19: 433-440.

Leffler, H., editor, (2004b) Special Issue on Galectins. *Glycoconj. J.* 19: 433-638.

Lowary, T. L. and Hindsgaul, O. (1994) Recognition of synthetic O-methyl, epimeric, and amino analogues of the acceptor α-L-Fucp-(1-2)-β-D-Galp-OR by the blood-group A and B gene-specified glycosyltransferases. *Carbohydr. Res.* 251:33-67.

Pieters, R. (2006) Inhibition and Detection of Galectins. *ChemBioChem.* 7: 721-728.

Sörme, P., Arnoux, P., Kahl-Knutsson, B., Leffler, H., Rini, J. M., Nilsson, U. J. (2005) Structural and thermodynamic studies on cation-Π interactions in lectin-ligand complexes: High-affinity galectin-3 inhibitors through fine-tuning of an arginine-arene interaction. *J. Am. Chem. Soc.* 127:1737-1743.

The invention claimed is:

1. A method for preparing a 3,3'-di-azido-thio-digalactoside of formula (10) comprising:
reacting a compound of formula (8) with a compound of formula (9) to form an azido compound of formula (10)

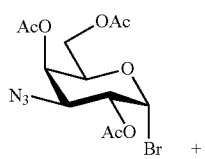

(8)

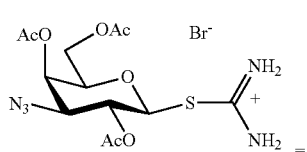

(9)

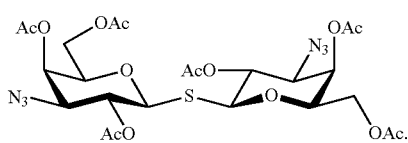

(10)

2. A method for preparing a thio-di-galactoside of the general formula (12)

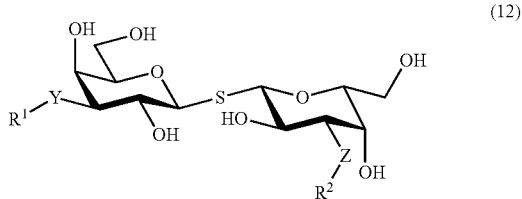

(12)

wherein
the configuration of one of the pyranose rings is β-D-galacto;
Y and Z are independently selected from being CONH or a 1H-1,2,3-triazole ring;
$R^1$ and $R^2$ are independently selected from the group consisting of:
a) an alkyl group of at least 4 carbons, an alkenyl group of at least 4 carbons, an alkynyl group of at least 4 carbons;
b) a carbamoyl group, a carbamoyl group substituted with an alkyl group, a carbamoyl group substituted with an alkenyl group, a carbamoyl group substituted with an alkynyl group, a carbamoyl group substituted with an aryl group, a carbamoyl group substituted with an substituted alkyl group, and a carbamoyl group substituted with an substituted aryl group;
c) a phenyl group substituted with at least one carboxy group, a phenyl group substituted with at least one halogen, a phenyl group substituted with at least one alkyl group, a phenyl group substituted with at least one alkoxy group, a phenyl group substituted with at least one trifluoromethyl group, a phenyl group substituted with at least one trifluoromethoxy group, a phenyl group substituted with at least one sulfo group, a phenyl group substituted with at least one hydroxy group, a phenyl group substituted with at least one carbonyl group, and a phenyl group substituted with at least one substituted carbonyl group;
d) a naphthyl group, a naphthyl group substituted with at least one carboxy group, a naphthyl group substituted with at least one halogen, a naphthyl group substituted with at least one alkyl group, a naphthyl group substituted with at least one alkoxy group, a naphthyl group substituted with at least one sulfo group, a naphthyl group substituted with at least one hydroxy group, a naphthyl group substituted with at least one carbonyl group, and a naphthyl group substituted with at least one substituted carbonyl group;
e) a quinoline, an isoquinoline, a pyridine, a pyrrole, a furan, or a thiophene group; and
f) a thienyl group, a thienyl group substituted with at least one carboxy group, a thienyl group substituted with at least one halogen, a thienyl thienyl group substituted with at least one alkoxy group, a thienyl group substituted with at least one sulfo group, a thienyl group substituted with at least one arylamino group, a thienyl group substituted with at least one hydroxy group, a thienyl group substituted with at least one halogen, a thienyl group substituted with at least one carbonyl group, and a thienyl group substituted with at least one substituted carbonyl group, the method comprising:

reacting a compound of formula (8) with a compound of formula (9) to form an azido compound of formula (10) which is then further substituted with the moieties Y, Z, R¹, and R²,

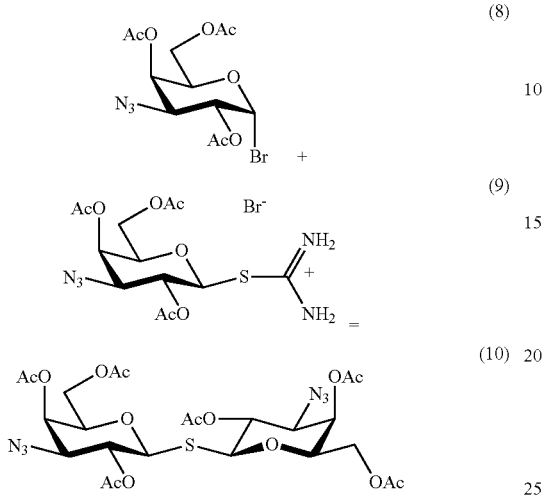

deprotecting the azido compound of formula (10); and substituting the moieties Y, Z, R¹, and R² onto the deprotected azido compound of formula (10) to prepare the compound of formula (12).

3. The method according to claim 2, wherein Y in formula (12) is CONH.

4. The method according to claim 3, wherein the CONH group constituting Y is linked via the N atom to the pyranose ring.

5. The method according to any one of claims 2-4, wherein Z is CONH.

6. The method according to claim 5, wherein the CONH group constituting Z is linked via the N atom to the pyranose ring.

7. The method according to claim 2, wherein Y in formula (12) is a 1H-1,2,3-triazole ring.

8. The method according to claim 7, wherein the 1H-1,2,3-triazole ring constituting Y is linked via the N1 atom to the pyranose ring.

9. The method according to claim 8, wherein R¹ is linked to the C4 atom of the 1H-1,2,3-triazole ring.

10. The method according to claim 2 or any one of claims 7-9, wherein Z in formula (12) is a 1H-1,2,3-triazole ring.

11. The method according to claim 10, wherein the 1H-1,2,3-triazole ring constituting Z is linked via the N1 atom to the pyranose ring.

12. The method according to claim 11, wherein R² is linked to the C4 atom of the 1H-1,2,3-triazole ring.

13. The method according to claim 2, wherein R¹ and R² are independently selected from the group consisting of a carbamoyl group, an alkylated carbamoyl group, an alkenylated carbamoyl group, an arylated carbamoyl group, a phenyl group substituted with at least one halogen group, a fluorinated phenyl group, a chlorinated phenyl group, a brominated phenyl group, an alkylated phenyl group, an alkenylated phenyl group, a trifluoromethylated phenyl group, a methoxylated phenyl group, a trifluoromethoxylated phenyl group, a naphthyl group, a naphthyl group substituted with at least one carboxy group, a naphthyl woo substituted with at least one halogen, a naphthyl group substituted with at least one alkyl group, a naphthyl group substituted with at least one alkoxy group, a naphthyl group substituted with at least one sulfo group, a napthyl group substituted with at least one hydroxy group, a naphthyl group substituted with at least one carbonyl group, and a naphthyl group substituted with at least one substituted carbonyl group, a thienyl group, a thienyl group substituted with at least one carboxy group, a thienyl group substituted with at least one halogen, a thienyl group substituted with at least one alkoxy group, a thienyl group substituted with at least one sulfo group, a thienyl group substituted with at least one arylamino group, a thienyl group substituted with at least one hydroxy group, a thienyl group substituted with at least one halogen, a thienyl group substituted with at least one carbonyl group, and a thienyl group substituted with at least one substituted carbonyl group.

14. The method according to claim 2, wherein R¹ is an alkylated carbamoyl group, a fluorinated phenyl group, or a thienyl group.

15. The method according to claim 2, wherein R² is an alkylated carbamoyl group, a fluorinated phenyl group, or a thienyl group.

16. The method according to claim 2, further comprising reacting bromine with a compound of formula (7)

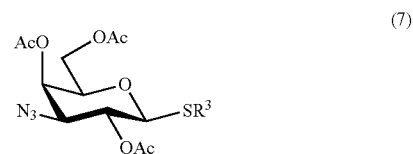

to form the compound of formula (8) prior to performing the reaction of the compound of formula (8) with the compound of formula (9), wherein R³ is selected from the group consisting of an alkyl group, an alkenyl group, an alkynyl group, a phenyl group, a substituted phenyl group, or an aryl group.

17. The method according to claim 16, further comprising reacting a compound of formula (6)

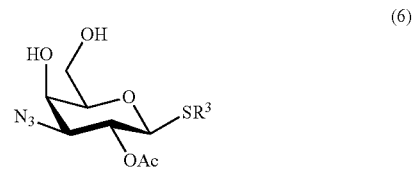

with acetic anhydride in pyridine to form a compound of formula (7) prior to the formation of the compound of formula (8), wherein R³ is selected from the group consisting of an alkyl group, an alkenyl group, an alkynyl group, a phenyl group, a substituted phenyl group, or an aryl group.

18. The method according to claim 17, further comprising reacting a compound of formula (5)

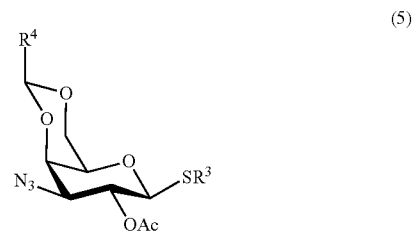

with acetic acid to form a compound of formula (6) prior to the formation of the compound of formula (7), wherein R³ and R⁴ are independently selected from the group consisting of an alkyl group, an alkenyl group, an alkynyl group, a phenyl group, a substituted phenyl group, or an aryl group.

19. The method according to claim 18, further comprising reacting a compound of formula (4)

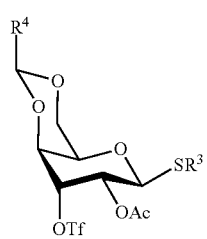

(4)

with $Bu_4N^+N_3^-$, or another azide source, to form a compound of formula (5) prior to the formation of the compound of formula (6), wherein $R^3$ and $R^4$ are independently selected from the group consisting of an alkyl group, an alkenyl group, an alkynyl group, a phenyl group, a substituted phenyl group, or an aryl group.

20. The method according to claim 19, further comprising reacting a compound of formula (3)

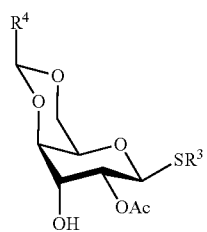

(3)

with $Tf_2O$ (trifluoromethanesulfonic anhydride) to form a compound of formula (4) prior to the formation of the compound of formula (5), wherein $R^3$ and $R^4$ are independently selected from the group consisting of an alkyl group, an alkenyl group, an alkynyl group, a phenyl group, a substituted phenyl group, or an aryl group.

21. The method according to claim 20, further comprising reacting a compound of formula (2)

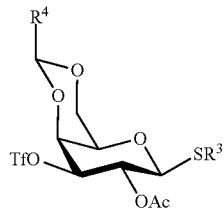

(2)

with $Bu_4N^+NO_2^-$ to form a compound of formula (3) prior to the formation of the compound of formula (4), wherein $R^3$ and $R^4$ are independently selected from the group consisting of an alkyl group, an alkenyl group, an alkynyl group, a phenyl group, a substituted phenyl group, or an aryl group.

22. The method according to claim 21, further comprising reacting a compound of formula (1)

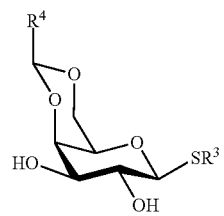

(1)

with $Tf_2O$ followed by acetylating reaction conditions to form a compound of the formula (2) prior to the formation of the compound of formula (3), wherein $R^3$ and $R^4$ are independently selected from the group consisting of an alkyl group, an alkenyl group, an alkynyl group, a phenyl group, a substituted phenyl group, or an aryl group.

* * * * *

UNITED STATES PATENT AND TRADEMARK OFFICE
CERTIFICATE OF CORRECTION

| | | |
|---|---|---|
| PATENT NO. | : 8,697,862 B2 | Page 1 of 1 |
| APPLICATION NO. | : 12/992328 | |
| DATED | : April 15, 2014 | |
| INVENTOR(S) | : Nilsson | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 339 days.

Signed and Sealed this
Twenty-first Day of July, 2015

Michelle K. Lee
*Director of the United States Patent and Trademark Office*